United States Patent
Schatz

[11] Patent Number: 5,951,568
[45] Date of Patent: Sep. 14, 1999

[54] OVER THE WIRE SINGLE OPERATOR CATHETER WITH WIRE STABILIZER

[76] Inventor: Richard A. Schatz, P.O. Box 8517, Rancho Santa Fe, Calif. 92067

[21] Appl. No.: 09/045,154

[22] Filed: Mar. 19, 1998

[51] Int. Cl.[6] .................................................. A61F 11/00
[52] U.S. Cl. ............................................ 606/108; 606/194
[58] Field of Search .................................... 606/108, 194, 606/205; 604/96, 102, 101, 103, 104, 106, 198, 920, 915, 164, 165, 77, 99, 100, 280; 600/585

[56] References Cited

U.S. PATENT DOCUMENTS

| | | |
|---|---|---|
| 2,574,840 | 11/1951 | Pieri et al. . |
| 3,467,101 | 9/1969 | Fogarty et al. . |
| 3,528,406 | 9/1970 | Jeckel et al. . |
| 3,789,841 | 2/1974 | Antoshkiw . |
| 3,906,938 | 9/1975 | Fleischhacker . |
| 4,033,331 | 7/1977 | Guss et al. . |
| 4,195,637 | 4/1980 | Grüntzig et al. . |
| 4,215,703 | 8/1980 | Willson . |
| 4,323,071 | 4/1982 | Simpson et al. . |
| 4,444,188 | 4/1984 | Bazell et al. . |
| 4,456,017 | 6/1984 | Miles . |
| 4,516,972 | 5/1985 | Samson . |
| 4,655,214 | 4/1987 | Linder . |
| 4,886,067 | 12/1989 | Palermo . |
| 5,490,859 | 2/1996 | Mische et al. ............................ 606/159 |
| 5,516,336 | 5/1996 | McInnes et al. ......................... 606/196 |
| 5,558,101 | 9/1996 | Cooks et al. ............................. 728/772 |

*Primary Examiner*—Michael Buiz
*Assistant Examiner*—Lien Ngo
*Attorney, Agent, or Firm*—Nydegger & Associates

[57] ABSTRACT

An over-the-wire catheter includes a catheter that is formed with a lumen for receiving a guidewire therethrough. A slit, which is formed along the guidewire lumen to provide external access into the lumen, extends at least part way along the length of the catheter. A connector, which is formed with an orifice for receiving the catheter therethrough, also includes a grip. In operation, the guidewire is pre-positioned as desired. An end of the guidewire is then passed through the orifice of the connector and is inserted into the guidewire lumen of the catheter. The distal end of the catheter is then inserted over the wire and through the orifice of the connector. Next, the grip on the connector is inserted through the slit and into the guidewire lumen for fixed engagement with the guidewire. The catheter is then advanced through the orifice of the connector and over the guidewire. As the catheter is advanced, the grip slides along the slit of the catheter lumen to maintain a fixed relationship between the guidewire and the connector.

18 Claims, 2 Drawing Sheets

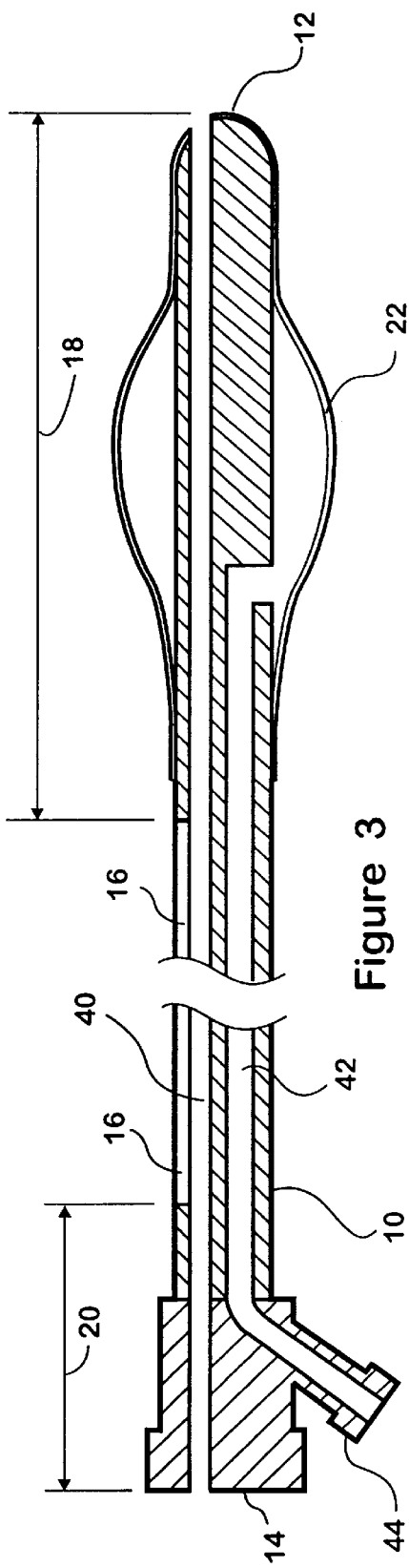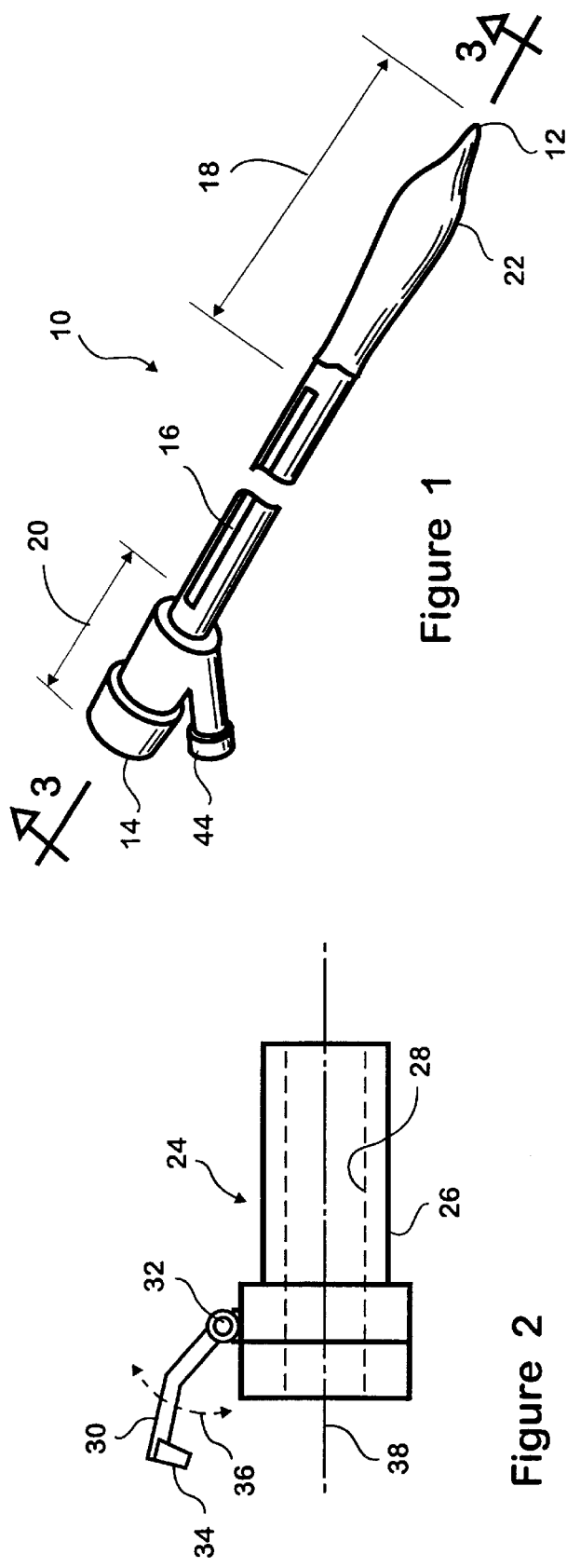
Figure 1
Figure 2
Figure 3

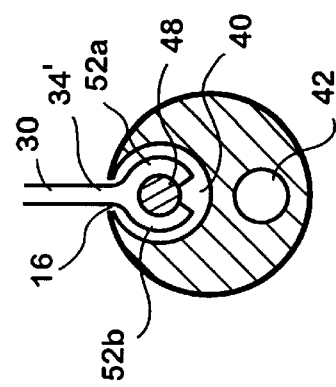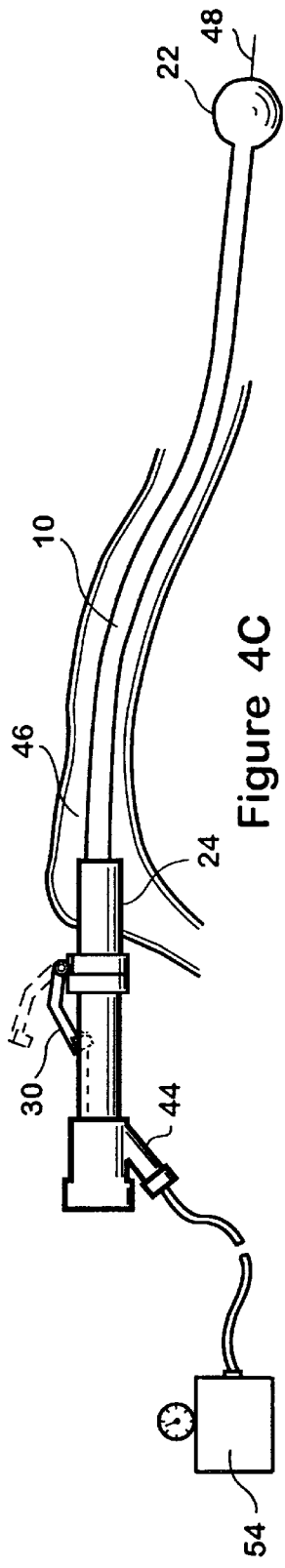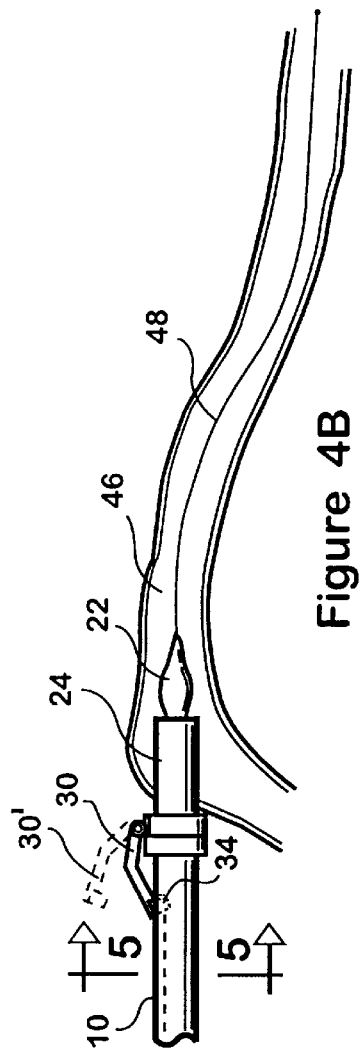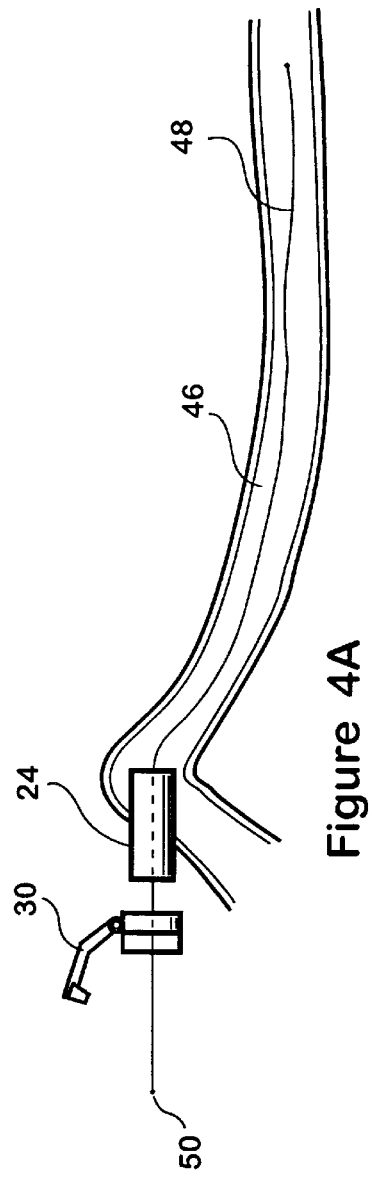
Figure 5
Figure 4C
Figure 4B
Figure 4A

OVER THE WIRE SINGLE OPERATOR CATHETER WITH WIRE STABILIZER

FIELD OF THE INVENTION

The present invention pertains generally to surgical devices. More particularly, the present invention pertains to interventional catheters which use guidewires for proper placement of the catheter in a vessel of a patient's cardiovascular system. The present invention is particularly, but not exclusively, useful as a device and method for advancing the catheter over an in situ guidewire.

BACKGROUND OF THE INVENTION

Several techniques for positioning medical devices in the cardiovascular systems of patients have been previously proposed in the pertinent art. In many instances, the object of these techniques is to advance a tool into the artery of a patient which is capable of accomplishing a desired task inside the artery. For example, in many of today's surgical procedures, medical devices such as catheter mounted angioplasty balloons, incisors, stents and artherectomy cutters are routinely introduced into patient's cardiovascular systems in accordance with prescribed protocols. One commonly used apparatus for introducing these devices is a guidewire.

Typically, whenever a guidewire is used for the purpose of introducing a medical device into the cardiovascular system of a patient, the guidewire is pre-positioned in situ. Normally this is done through an introducer sheath or an introducer catheter which is used to establish an access site into the cardiovascular system of the patient. The catheter mounted medical device is then subsequently advanced through the introducer (guiding catheter) and over the guidewire. During the advancement of the catheter over the wire, however, it is extremely important for the physician to maintain positive control over both the stability of the guidewire and the advancement of the catheter. Further, it is important that the means for controlling the stability of the guidewire and the means for controlling the advancement of the catheter be relatively close to each other and relatively near the introductory access site into the patient.

One solution to the control problem for an over-the-wire catheter is to provide a guidewire of sufficient length so that any extracorporeal portion of the guidewire is longer than the catheter that is being introduced over the wire. This, however, can be cumbersome and may require manipulation of the system at a substantial distance from introductory access site. A solution to this problem has been the use of so-called monorail catheters. The monorail catheters in use today have a relatively short guidewire lumen which is located near the distal tip of the catheter so that the guidewire can be extracorporeal separated from the catheter. This arrangement, however, still requires the physician to effectively control both the guidewire and the catheter.

In light of the above, it is an object of the present invention to provide an over-the-wire catheter system which effectively reduces the physician's control requirements to only advancement of the catheter. Another object of the present invention is to provide an over-the-wire catheter system which stabilizes the position of the guidewire during advancement of the catheter over the wire. Still another object of the present invention is to provide an over-the-wire catheter system which incorporates the guidewire, the introducer, and the catheter into a cooperative system which allows for accurate placement of the catheter into the cardiovascular system of a patient. Yet another object of the present invention is to provide an over-the-wire catheter system which is simple to use, relatively easy to manufacture, and comparatively cost effective.

SUMMARY OF THE PREFERRED EMBODIMENTS

An over-the-wire catheter system of the present invention includes a catheter which has a guidewire lumen that preferably extends from its distal end to its proximal end. In addition to the guidewire lumen, a slit is formed into the catheter body which is oriented to extend part of the way along the guidewire lumen. More specifically, the slit is provided to establish a pathway for external access into the guidewire lumen. Preferably, the slit terminates at a first distance from the distal end of the catheter, and at a second distance from the proximal end of the catheter.

A connector body is provided for the over-the-wire catheter system which is formed with an orifice that passes through the connector body. As a practical matter, the connector body can be part of an introducer sheath or it can be a Tuoehy Borts type y-connector. In either case, the system of the present invention includes a stabilizer arm which is hingedly mounted on the connector body, and a grip is attached to the free end of the stabilizer arm. As intended for the present invention, the grip may be a magnet or some mechanical structure which is capable of grasping and fixedly holding a guidewire. For example, the grip may be a snap which is formed with a pair of parallel legs that extend from said stabilizer arm. If so, for this embodiment of the grip, the legs should be distanced from each other to establish a gap that is dimensioned to create a fixed interference fit with said guidewire when said grip is engaged therewith.

In the operation of the over-the-wire catheter system of the present invention, a guidewire is first pre-positioned in situ. Normally, the positioning of the guidewire will be accomplished through an introducer sheath or guiding catheter. As indicated above, this guiding catheter or introducer can also, with appropriate modifications, be used as the connector body of the present invention. In any event, the in situ guidewire will be positioned to also pass through the orifice of the connector body.

Once the guidewire is in place, and is passing through the orifice of the connector body, the guidewire is inserted into the guidewire lumen at the distal end of the catheter. The distal end of the catheter is then advanced along the guidewire and through the orifice of the connector body. This advancement continues until the distal portion of the slit in the catheter just enters the orifice of the connector body. At that point the advancement of the catheter over the guidewire is stopped and the grip is engaged with guidewire.

To engage the grip of the connector body with the guidewire, the operator simply swings the stabilizer arm in a manner which will cause the grip to be inserted through the slit of the catheter and into the guidewire lumen. Depending on the type of grip used, the grip may either grasp the guidewire, as in the case of the snap-fit grip mentioned above, or the grip may attach to the guidewire, as in the case of a magnet grip. Further, it is contemplated by the present invention that the grip may be a mechanically actuated claw or some other mechanical fastener which will secure the grip to the guidewire. The important consideration is that grip be insertable through the slit in the catheter and that once inserted the grip will be steadfastly secured to the guidewire to prevent relative movement between the guidewire and the connector body.

With the guidewire securely fastened to the connector body, the catheter can then be further advanced along the guidewire and through the orifice of the connector body. As the catheter is advanced thusly, the grip slides along the slit of the catheter lumen to maintain a fixed relationship between the guidewire and the connector body. Accordingly, only the catheter needs to be controlled.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a side elevation view of the catheter of the present invention;

FIG. 2 is a side elevation view of the connector body of the present invention with portions shown in phantom for clarity;

FIG. 3 is a cross-sectional view of the catheter of the present invention as seen along the line 3—3 in FIG. 1;

FIG. 4A is a schematic view of the connector body of the present invention positioned over an in situ guidewire;

FIG. 4B is a schematic view of the catheter of the present invention interconnected with the connector body of the present invention;

FIG. 4C is a schematic view of the catheter of the present invention advanced into position over the guidewire; and FIG. 5 is a cross sectional view of the system of the present invention as seen along the line 5—5 in FIG. 4B.

DESCRIPTION OF THE PREFERRED EMBODIMENT

Referring initially to FIG. 1 an over-the-wire catheter for use with the present invention is shown and generally designated 10. In FIG. 1 it will be seen that the catheter 10 has a distal end 12 and a proximal end 14. Also in FIG. 1 it can be seen that the catheter 10 includes a slit 16 which extends longitudinally (axially) along the length of the catheter 10. More specifically, it will be seen that the slit 16 terminates at a first distance 18 from the distal end 12 of the catheter 10, and at a second distance 20 from the proximal end 14 of the catheter 10. By way of example, the catheter 10 is shown in FIG. 1 to include an inflatable balloon 22 which is located within the first distance 18 between the slit 16 and the distal end 12.

In FIG. 2, the connector of the present invention is shown and generally designated 24. As shown, the connector 24 includes a connector body 26 which is formed with an orifice 28 (shown in phantom). The connector 24 also includes a stabilizer arm 30 which is attached to the connector body 26 by a hinge 32 substantially as shown. As also shown, a grip 34 is mounted on the free end of the stabilizer arm 30. Preferably, the hinge 32 is able to pivot in the directions indicated by the arrows 36 about an equilibrium position, as shown in FIG. 4A, wherein the grip 34 is normally positioned at a distance from the centerline 38 of the orifice 28. For these purposes, a preferred structure for the connector 24 is one wherein the connector 24 is made of a plastic type material, and the hinge 32 is a narrowed portion of the stabilizer arm 30. Such a hinge 32 is sometimes referred to in the pertinent art as a "living hinge" or an "integral hinge".

FIG. 3 shows that the catheter 10 of the present invention includes a guidewire lumen 40 which extends along the entire length of the catheter 10 from the proximal end 14 to the distal end 12. Also shown is that the slit 16 provides external access into the guidewire lumen 40 for a substantial portion of the length of the catheter 10. As indicated above, the slit 16, and thus also external access into the guidewire lumen 40, terminates respectively at the first distance 18 from distal end 12 and at the second distance 20 from proximal end 14 of catheter 10. By way of example, the catheter 10 is shown to be a balloon catheter. Accordingly, the catheter 10 includes an inflation lumen 42 which establishes a pathway for fluid communication from a balloon port 44 at the proximal end 14 of catheter 10 to the balloon 22 at the distal end 12 of the catheter 10.

Operation

In the operation of the over-the-wire catheter system of the present invention, extracorporeal access is first established into the cardiovascular system of the patient. In most instances, this access will be into a vessel of the cardiovascular system, such as into an artery 46 as shown in FIG. 4A In the case where the connector 24 is to also be used as an introducer sheath, the connector body 26 of connector 24 can be used to penetrate into the artery 46 as shown. A guidewire 46 is then passed separately through the orifice 28 of the connector body 26 and pushed through the artery 46 until it is positioned in situ as desired by the physician. For purposes of discussing the present invention, consider the guidewire 48 shown in FIG. 4B to be properly positioned.

Once the guidewire 48 has been positioned in the artery 46 of a patient, the extracorporeal (proximal) end 50 of the guidewire 48 is inserted into the guidewire lumen 40 at the distal end 12 of the catheter 10. At this point the catheter 10 is advanced through the connector 24 until the grip 34 is positioned over the slit 16 of catheter 10. As shown in FIG. 4B, with the grip 34 positioned over the slit 16, the stabilizer arm 30 of connector 24 is rotated or pivoted from its equilibrium position (shown in phantom and designated 30' in FIG. 4B) to insert the grip 34 through the slit 16 and into engagement with the guidewire 48.

With the grip 34 engaged with the guidewire 48, the guidewire 48 is stationarily fixed relative to the connector 24. On the other hand, the catheter 10 is free to move along the guidewire 48 as the grip 34 slides freely along the slit 16 of the catheter 10. In this way the catheter 10 can be advanced along the guidewire 48 while the guidewire 48 is held stationary by the connector 24. Consequently, with this cooperation of structure, the physician is concerned only with control over the catheter 10 as the catheter 10 is advanced into its operative position over the in situ guidewire 48. As best appreciated by reference to FIGS. 1 and 3, the grip 34 will hold the guidewire 48 until the catheter 10 has been advanced to a point where the grip 34 is at the distance 20 from the proximal end 14 of catheter 10. At that point, the grip 34 can be released from the guidewire 48 and the catheter 10 can continue to be used as an over-the-wire catheter.

For one embodiment of the present invention, the grip 34 may be a permanent magnet which will magnetically attach and hold itself on the guidewire 48. Other embodiments are, of course, also possible for the grip 34. One such alternate embodiment is shown in FIG. 5. In FIG. 5 the grip 34' is shown to include a pair of curved legs 52a and 52b which extend substantially parallel to each other from the stabilizer arm 30. As shown, the legs 52a and 52b form a gap between them for receiving the guidewire 48 therein. More specifically, for this embodiment of the present invention, the distance between the legs 52a,b, and therefore the gap that is formed, can be dimensioned to create a snap-fit connection between the grip 34' and the guidewire 48. Further, to help ensure a secure attachment of the grip 34' on the guidewire 48, the legs 52a,b can be dimensioned relative to each other to be slightly closer to each other than the diameter of the guidewire 48. In this way, an interference type fit can be established.

While the particular over-the-wire single operator catheter with wire stabilizer as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A catheter advanceable over an in situ guidewire which comprises:
   a catheter formed with a lumen for receiving the guidewire therein, said catheter being formed with a longitudinal slit oriented along said lumen of said catheter to provide external access to said guidewire in said lumen through said slit; and
   a connector means slidingly attached to said catheter for movement thereon and engageable with the guidewire through said slit to fixedly hold the guidewire to said connector means as said catheter is advanced along the guidewire.

2. A catheter as recited in claim 1 wherein said connector means comprises:
   a connector body formed with an orifice for receiving said catheter therethrough;
   a stabilizer arm hingedly mounted on said connector body; and
   a grip attached to said stabilizer arm for selective insertion through said slit and into said lumen of said catheter for engagement with said guidewire to fixedly hold said guidewire to said connector body as said catheter is advanced through said orifice of said connector body and along said guidewire.

3. A catheter as recited in claim 2 wherein said catheter is formed with an inflatable balloon and an inflation lumen, and said device further comprises a pump connected in fluid communication with said inflation lumen for inflating said balloon.

4. A catheter as recited in claim 2 wherein said catheter has a distal end and a proximal end and wherein said slit terminates at a first distance from said distal end and at a second distance from said proximal end and wherein said stabilizer arm is connected with said connector body by an integral hinge.

5. A device as recited in claim 2 wherein said grip is a magnet, said magnet being magnetically secured to said guidewire when said grip is engaged therewith.

6. A device as recited in claim 2 wherein said grip is a snap formed with a pair of substantially parallel legs extending from said stabilizer arm, said legs being distanced from each other to establish a gap therebetween with said gap being dimensioned to create a fixed interference fit with said guidewire when said grip is engaged therewith.

7. A medical device which comprises:
   a guidewire;
   a catheter formed with a lumen for receiving said guidewire therethrough, said catheter being formed with a longitudinal slit oriented along said lumen of said catheter to provide external access into said lumen through said slit;
   a connector formed with an orifice for receiving said catheter and being slidingly mounted on said catheter for movement thereon;
   a stabilizer arm hingedly mounted on said connector; and
   a grip attached to said stabilizer arm for selective insertion through said slit and into said lumen of said catheter for engagement with said guidewire to fixedly hold said guidewire to said connector as said catheter is advanced through said orifice of said connector body and along said guidewire.

8. A device as recited in claim 7 wherein said catheter is formed with an inflatable balloon and an inflation lumen, and said device further comprises a pump connected in fluid communication with said inflation lumen for inflating said balloon.

9. A device as recited in claim 7 wherein said catheter has a distal end and a proximal end and wherein said slit terminates at a first distance from said distal end and at a second distance from said proximal end.

10. A device as recited in claim 7 wherein said connector includes a connector body and said stabilizer arm is connected with said connector body by an integral hinge.

11. A device as recited in claim 7 wherein said grip is a magnet, said magnet being magnetically secured to said guidewire when said grip is engaged therewith.

12. A device as recited in claim 7 wherein said grip is a snap formed with a pair of substantially parallel legs extending from said stabilizer arm, said legs being distanced from each other to establish a gap therebetween with said gap being dimensioned to create a fixed interference fit with said guidewire when said grip is engaged therewith.

13. A method for using a device which includes a catheter having a distal end and a proximal end and formed with a lumen, said catheter having a longitudinal slit oriented on the catheter along the lumen to provide external access thereto through the slit, a connector formed with an orifice and being slidingly mounted on said catheter for movement thereon, and having a grip hingedly mounted thereon, the method which comprises the steps of:
   positioning a guidewire in situ;
   placing the connector body over the guidewire with the guidewire passing through the orifice of the connector;
   introducing the guidewire into the lumen of the catheter;
   moving the distal end of the catheter over the guidewire and through the orifice of the connector;
   selectively inserting the grip through the slit of the catheter for engagement of the grip with the guidewire to fixedly hold the guidewire to the connector; and
   advancing the catheter along the guidewire.

14. A method as recited in claim 13 wherein said catheter is formed with an inflatable balloon and an inflation lumen, and said device further comprises a pump connected in fluid communication with said inflation lumen for inflating said balloon.

15. A method as recited in claim 13 wherein said slit terminates at a first distance from said distal end and at a second distance from said proximal end.

16. A method as recited in claim 13 wherein said grip is a magnet, said magnet being magnetically secured to said guidewire when said grip is engaged therewith.

17. A device as recited in claim 13 wherein said grip is a snap formed with a pair of substantially parallel legs extending from said stabilizer arm, said legs being distanced from each other to establish a gap therebetween with said gap being dimensioned to create a fixed interference fit with said guidewire when said grip is engaged therewith.

18. A catheter advanceable over an in situ guidewire which comprises:

a catheter formed with a lumen for receiving the guidewire therein, said catheter being formed with a longitudinal slit oriented along said lumen of said catheter to provide external access to said guidewire in said lumen through said slit;

a connector body formed with an orifice for receiving said catheter therethrough and being slidingly attached to said catheter for movement thereon;

a stabilizer arm hingedly mounted on said connector body; and a magnet attached to said stabilizer arm for selective insertion through said slit and into said lumen of said catheter for engagement with said guidewire to fixedly hold said guidewire to said connector body as said catheter is advanced through said orifice of said connector body and along said guidewire, said magnet being magnetically secured to said guidewire when engaged therewith.

* * * * *